(12) United States Patent
Twitty et al.

(10) Patent No.: US 10,226,518 B2
(45) Date of Patent: Mar. 12, 2019

(54) UBIQUITINYLATED PROTEINS

(71) Applicants: UBIVAC, LLC, Portland, OR (US); PROVIDENCE HEALTH & SERVICES—OREGON, Portland, OR (US)

(72) Inventors: Christopher Twitty, Solana Beach, CA (US); Erik LeShane, Portland, OR (US); Bernard Fox, Portland, OR (US); Hong-Ming Hu, Portland, OR (US); Guangjie Yu, Hohhot (CN)

(73) Assignees: UbiVac, LLC, Portland, OR (US); Providence Health & Science—Oregon, Portland, OR (US)

( * ) Notice: Subject to any disclaimer, the term of this patent is extended or adjusted under 35 U.S.C. 154(b) by 73 days.

(21) Appl. No.: 14/512,322

(22) Filed: Oct. 10, 2014

(65) Prior Publication Data

US 2015/0104477 A1    Apr. 16, 2015

Related U.S. Application Data

(60) Provisional application No. 61/890,054, filed on Oct. 11, 2013.

(51) Int. Cl.
*A61K 39/00* (2006.01)
*C12P 21/00* (2006.01)

(52) U.S. Cl.
CPC .......... *A61K 39/0011* (2013.01); *C12P 21/00* (2013.01)

(58) Field of Classification Search
None
See application file for complete search history.

(56) References Cited

U.S. PATENT DOCUMENTS

2009/0220530 A1* 9/2009 Hu .................... A61K 39/0011
424/184.1

FOREIGN PATENT DOCUMENTS

| JP | 2007244394 A | 9/2007 |
| JP | 2012039877 A | 3/2012 |
| WO | 2012027696 A1 | 3/2012 |

OTHER PUBLICATIONS

Yao et al (Genes and Cancer 1:779-786, 2010.*
Twitty et al (Cancer Res, 17:6467, 2011.*
HEK293 cell line fact sheet (www.HEK293.com; Download 2016.*
Definition of DRibble vaccine on National Cancer Institute Website, download 2017.*
Twitty et al (Cancer Res, 17:6467, 2011 (Year: 2011).*
Tan et al (Human Mole Genetics, 17:431-439, 2008 (Year: 2008).*
Li, Yuhuan, et al. "Cross-presentation of tumor associated antigens through tumor-derived autophagosomes", Autophagy, vol. 5, No. 4, May 2009, pp. 576-577.
ISA Korean Intellectual Property Office, International Search Report and Written Opinion of PCT/US2014/060180, dated Jan. 15, 2015, 10 pages.
Li, Yuhuan, et al. "Tumor-Derived Autophagosome Vaccine: Mechanism of Cross-Presentation and Therapeutic Efficacy", Clinical Cancer Research, vol. 17, No. 22, Nov. 15, 2011, pp. 7047-7057.
Li, Weixia, et al. "Tumor-Derived Autophagosomes (DRibbles) induce B Cell Activation in a TLR2-MyD88 Dependent Manner", PloS one, vol. 8, No. 1, Jan. 2013, 12 pages.
Ye, Wei, et al. "Cross-presentation of viral antigens in dribbles leads to efficient activation of virus-specific human memory t cells", Journal of Translational Medicine, vol. 12, No. 1, Apr. 2014, 12 pages.
Bakowska-Zywicka, K. et al., "Ribophagy—the novel degradation system of the ribosome," Biotechnologia, vol. 2009, No. 1, Available as Early as Jan. 1, 2009, 5 pages.
Twitty, C. et al., "Autophagosome vaccine cross-protects and breaks tumor immunology paradigm: a p62-dependent mechanism?," Journal of Immunology, vol. 182, Supplement 1, Apr. 1, 2009, Retrieved Online at http://www.jimmunol.org/content/182/1_Supplement/41.41, 4 pages.
Ren, H. et al., "Therapeutic Antitumor Efficacy of B Cells Loaded With Tumor-derived Autophagasomes Vaccine (DRibbles)," Journal of Immunotherapy, vol. 37, No. 8, Oct. 2014, 11 pages.
Turco, E et al., "Insights into autophagosome biogenesis from in vitro reconstitutions," Journal of Structural Biology, vol. 196, No. 1, Oct. 2016, Published Online May 30, 2016, 8 pages.
European Patent Office, Extended European Search Report Issued in Application No. 14851719.6, dated May 16, 2017, Germany, 8 pages.
Japanese Patent Office, Office Action Issued in Application No. 2016521645, dated Jun. 19, 2018, 7 pages.

* cited by examiner

*Primary Examiner* — Lei Yao
(74) *Attorney, Agent, or Firm* — McCoy Russell LLP

(57) ABSTRACT

A method of inducing a specific immune response in a mammal, comprising: providing a first composition comprising isolated ubiquitinylated proteins in solution in the absence of membrane bound organelles, the isolated ubiquitinylated proteins comprising one or more specific antigens, and further comprising a threshold quantity of polyubiquitinylated short-lived proteins and polyubiquitinylated defective ribosomal products. The isolated ubiquitinylated proteins are affinity-purified from tumor-derived cells grown in culture, the tumor-derived cells being inhibited from degrading ubiquitinylated proteins via the proteasome while being grown in culture. In this way, highly immunogenic short-lived proteins and defective ribosomal products may be loaded onto dendritic cells for cross-presentation and priming of antigen-specific T cells restricted by either classical or non-classical MHC.

11 Claims, 12 Drawing Sheets

UBIQUITINYLATED PROTEINS

CROSS REFERENCE TO RELATED APPLICATIONS

The present application claims priority to U.S. Provisional Patent Application No. 61/890,054, entitled "Ubiquitinylated Proteins," filed Oct. 11, 2013, the entire contents of which are hereby incorporated by reference for all purposes.

FIELD

This application relates to isolated ubiquitinylated protein compositions and methods of stimulating, enhancing, or facilitating an immune response by administration of isolated-ubiquitinylated protein products on their own or in conjunction with complementary therapeutics.

BACKGROUND AND SUMMARY

Cross-presentation of exogenous antigens by host professional antigen-presenting cells (APCs) plays a pivotal role in the initiation and development of T cell immune responses to tumor associated antigens, including self or mutated self-antigens derived from tumor cells, and foreign antigens derived from infectious agents. Prospective cancer vaccines have been developed that attempt to harness the cross-presentation of exogenous antigens to illicit a specific immune response against a tumor.

Autophagy is a cellular process in which portions of the cytoplasm are sequestered by double membrane vesicles termed autophagosomes that range in size from 0.5-2 μm. The contents of these autophagosomes are degraded in a lytic compartment, which facilitates the turnover of long-lived proteins and is critical for maintaining the pool of amino acids needed for anabolism. A key marker of the induction of autophagy is the conversion of the cytosolic form of microtubule-associated protein 1 light chain 3 (LC3-I) via a series of ubiquitin-like conjugation steps to the lipidated form (LC3-PE) that is tightly associated with autophagosomes. A recently described protein, p62/SQSTM1 (sequestosome or p62), binds both polyubiquitin and LC3 and thus facilitates degradation of ubiquitinated proteins via autophagy. Interaction of LC3 with p62 has added a layer of complexity to the autophagic network and suggests that this bulk degradation process may be more selective than previously appreciated.

Autophagy in tumor cells is important for efficient cross-presentation and subsequent induction of tumor immunity in a B16 melanoma model. Cross-presentation is significantly inhibited when autophagy is blocked, and increased when autophagy is promoted. Additionally, autophagosome-containing vesicles, termed DRibbles (DRiPs in blebs) isolated from tumors served as a potent antigen source in cross-presentation assays and in vivo vaccine studies. An important part of the process of generating the autophagosome-containing (DRibble) vaccine is the treatment of cells with bortezomib, which blocks the proteasome and results in an accumulation of ubiquitinated (Ub) proteins.

However, the inventors herein have recognized that the methods for production and isolation of DRibbles disclosed in the prior art may be insufficient to produce and isolate an enriched population of autophagosomes and their component material to be further utilized as an effective vaccine. Data points to ubiquitinated proteins, such as SLiPs and DRiPs, coupled with a chaperone (p62) as being responsible for the vaccine's potency. By isolating the ubiquitinated proteins, the highly-immunogenic portion of the autophagosome may be concentrated and effectively packaged as an immunogenic compound.

In one example, a method of inducing a specific immune response in a mammal, comprising: providing a first composition comprising isolated ubiquitinylated proteins in solution in the absence of membrane bound organelles, the isolated ubiquitinylated proteins comprising one or more specific antigens, and further comprising a threshold quantity of polyubiquitinylated short-lived proteins and polyubiquitinylated defective ribosomal products. The isolated ubiquitinylated proteins are affinity-purified from tumor-derived cells grown in culture, the tumor-derived cells being inhibited from degrading ubiquitinylated proteins via the proteasome while being grown in culture. In this way, highly immunogenic short-lived proteins and defective ribosomal products may be loaded onto dendritic cells for cross-presentation and priming of antigen-specific T cells restricted by either classical or non-classical MHC.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTIONS OF THE DRAWINGS

FIGS. 1A-1B schematically show cellular pathways for trafficking ubiquitinylated proteins in the presence and absence of proteasome inhibitors.

FIG. 2 schematically shows example ubiquitin binding proteins.

FIG. 3A schematically shows a GFP-fusion protein usable to affinity purify ubiquitinylated proteins.

DETAILED DESCRIPTION

This detailed description relates to compositions for and methods of inducing a specific immune response in a mammal. In particular, the description relates to compositions comprising isolated ubiquitinylated protein including one or more specific antigens. For example, ubiquitinylated protein may be isolated from tumor-derived cells inhibited from degrading ubiquitinylated protein at the proteasome. The isolated ubiquitinylated protein may include highly immunogenic antigens such as short-lived proteins and defective ribosomal products, which may be directly injected into mammals, or may be co-cultured with dendritic cells and/or T cells to derive cell populations that may be provided as a vaccine or as another immunological composition.

A highly desirable approach to fighting cancer includes developing effective therapeutic cancer vaccines capable of stimulating a broad-spectrum anti-tumor T cell response against multiple tumor rejection antigens that are expressed or overexpressed by many types of cancerous cells but not expressed by normal, healthy cells. As the identities of the antigens which are true rejection antigens remain unknown, an indirect approach to enrich these tumor-rejection antigens is expected to aid in the development of effective therapeutic cancer vaccines. In addition to over-expressed, non-mutated, short-live antigens that may serve as tumor-rejection antigens, many cancer cells produce unique proteins or mis-translated proteins that are either mutations, errors in transcription, translation and/or posttranslational modifications. These proteins are short-lived and marked for proteasome dependent degradation. This detailed description discloses a novel approach to isolate and enrich tumor rejection antigens using universal poly-ubiquitin tags for proteasome-mediated degradation. Isolated ubiquitinylated proteins are able to stimulate antigen-specific T cells and elicit antitumor T cell-mediated immune responses. Indeed, vaccination with these proteins was capable of mediating tumor regression of established tumor in preclinical model of breast cancer.

Figure 1B:
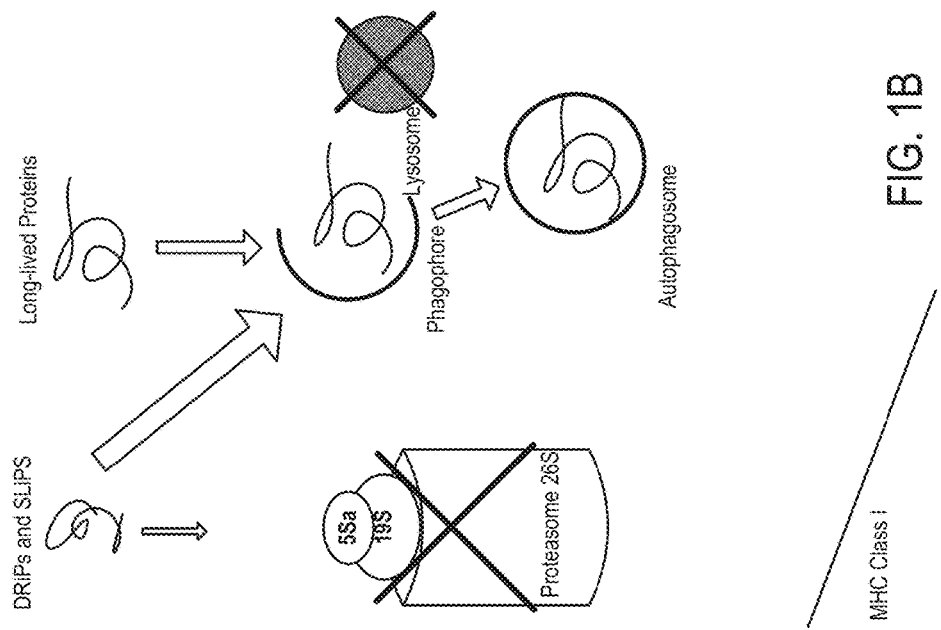
Figure 1A:
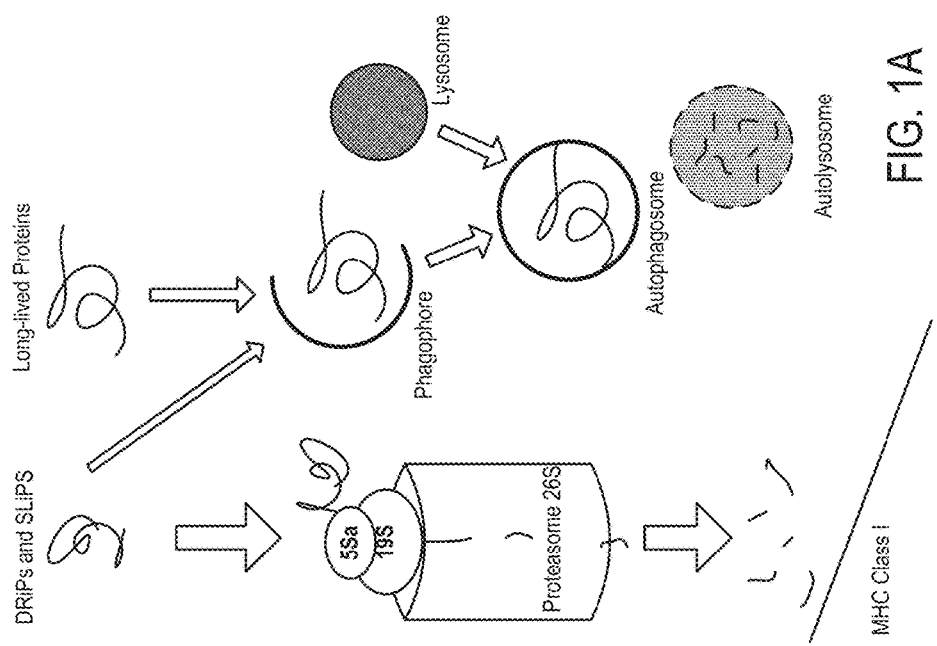

FIGS. 1A and 1B schematically show cellular pathways for trafficking ubiquitinylated proteins in the presence and absence of proteasome inhibitors. Proteins may be targeted for degradation by either autophagy pathways or proteasomal pathways. Typically, short lived proteins (SLiPs) and defective ribosomal proteins (DRiPs) are modified with a poly-ubiquitin tag and escorted by a heat shock protein (such as HSP-90) to the proteasome for degradation. The proteasome-mediated protein degradation pathway plays an important role in regulating cell signaling and in T cells in providing peptides for direct cell-surface presentation via MHC-I restricted antigen presentation.

Longer lived proteins that are damaged or misfolded are often disposed of via an autophagy pathway. Proteins and damaged organelles are engulfed by phagophores, which then fuse with lysosomes, evolving into autophagosomes. In antigen presenting cells, autophagy plays an important role in MHC-II restricted antigen presentation for both endogenous and exogenous antigens. In phagocytes, autophagy is required for Toll-like receptor-mediated recognition and activation of innate immune responses.

HSP-90 associated peptides, such as SLiPs and DRiPs include highly-immunogenic peptides. However, they are rapidly degraded by the proteasome, and thus not necessarily efficiently cross-presented. By blocking the proteasome with an inhibitor (such as bortezomib), SLiPs and DRiPs may be protected from proteasomal degradation and shunted into the autophagy pathway. If autophagy is also inhibited (such as by ammonium chloride) the SLiPs and DRiPs may be affinity-purified and used as an immunogenic compound.

Figure 2:
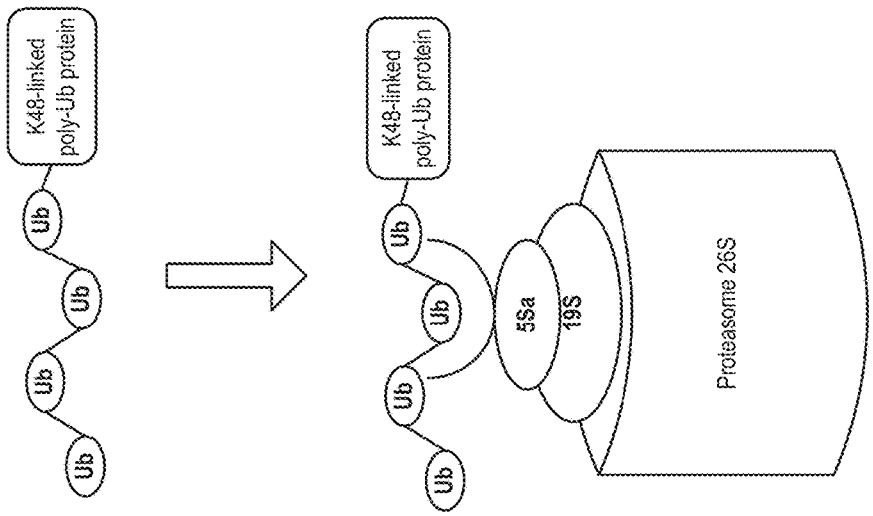
Figure 2:
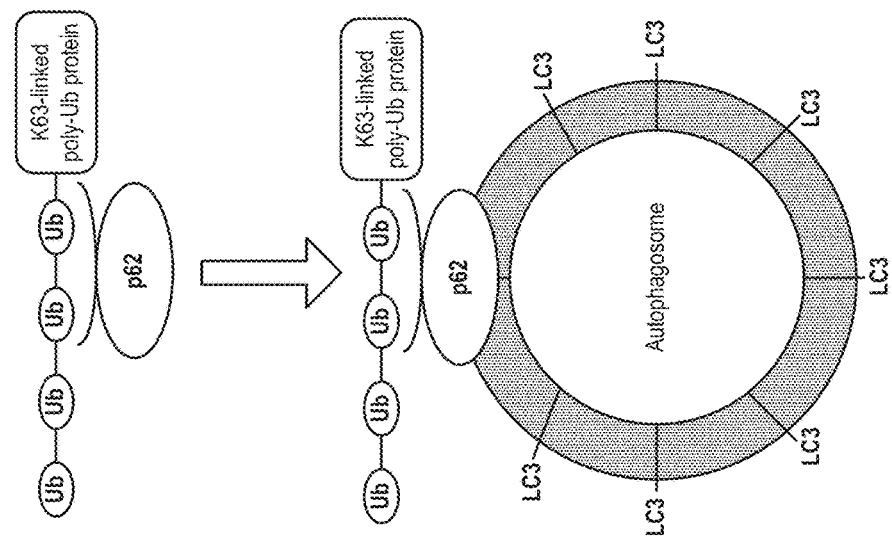
Figure 2:
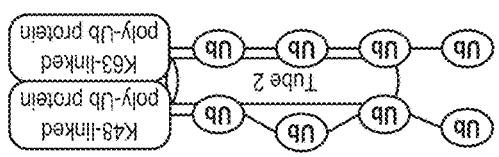
Figure 2:
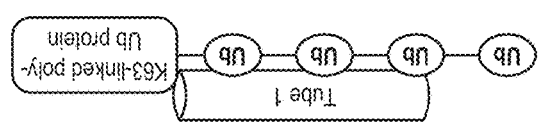

FIG. 2 shows example ubiquitin binding proteins. The specific lysine (K) linkage on the C-terminus of each monomer of a polyubiquitin chain dictates the fate of a tagged protein. The most abundant polyubiquitin chains are K48 linkages, which adopt a closed conformation and serve as a signal for target protein degradation by S5a, a component of the regulatory complex (19S) of the 26S proteasome. The next most common polyubiquitin linkages, K63, adopt an extended linear conformation that can serve as a non-proteasome docking site. K63 linked proteins have recently been described to play a role in tumorigenesis and neurodegenerative diseases. p62 is an endogenous K63 binding protein which plays a role in shuttling these proteins to autophagosomes. p62 may also bind K48 linked proteins. When the proteasome is blocked, and the concentration of K48 linked proteins increases, p62 may shuttle K48 linked proteins to autophagosomes as well as K63 linked proteins. Recombinant S5a and p62 may thus be utilized to affinity purify poly-ubiquitinylated proteins from cell lysates. Other ubiquitin binding proteins, such as TUBES, NEMO, Optineurin, TOLLIP, TOM1, Vx3, etc. may be recombinantly expressed with an affinity tag to enable efficient retrieval of bound ubiquitinylated proteins. Herein, S5a and Vx3 containing constructs are used to isolate ubiquitinylated proteins from cell lysates; however, other such constructs may be used. In particular, K48 and K63 specific proteins, antibodies, and/or combinations thereof may be used to isolate specific populations of ubiquitinylated proteins for downstream applications.

EXAMPLE 1

Stimulation of Naïve T-cells by Cross-presentation of Isolated Ubiquitinylated Proteins Cross-presentation was identified as a means by which antigens can be presented by cells in which they were not synthesized, thus obviating direct presentation as the sole mechanism to prime an immune response. These findings were expanded by the demonstration that cross-presentation of melanoma antigens during vaccination was essential for the generation of an effective anti-tumor immune response. One component of cross-presentation that has been debated and still remains unknown is the source of antigen and the method of its delivery to professional antigen-presenting cells (APC). While some groups have shown that the source of antigen is cellular protein, others argue that it is peptides chaperoned by heat shock proteins (HSPs). Further, it has been demonstrated that cross-priming may result from both the donation of proteasome substrates as well as stable cytosolic peptides in conjunction with HSP90. Experiments using both short-lived model antigen systems as well as inhibitors of protein translation indicate that short-lived proteins (SLiPs) and/or defective-ribosomal products (DRiPs) are an integral component of the antigen pool associated with autophagy-dependent cross-priming. This pool of antigen is typically cross-presented inefficiently because the short half-life of SLiPs prevents their donation to an APC. Interestingly, it is this temporal nature of SLiPs that allows them to make up a majority of the peptide:MHC complexes on the surface of cells, as they are quickly degraded by the proteasome and loaded onto MHC Class I molecules by TAP1/2. Treating tumors with a proteasome inhibitor (bortezomib) stabilizes these temporal proteins and shunts them into the other major degradative pathway, the autophagosomal/lysosomal pathway.

Figure 3B:
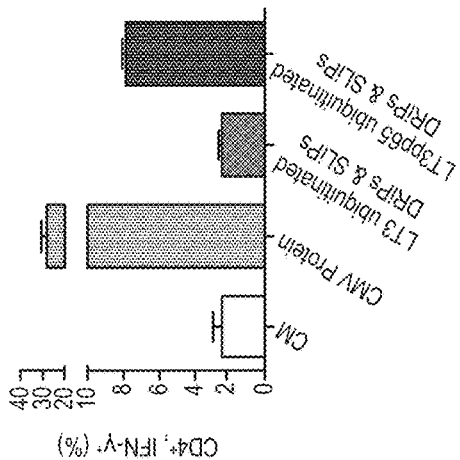
FIG. 3B is a digital image showing a fluorescent image for isolated ubiquitinylated protein bound to a Vx3-GFP-fusion protein.
Figure 3A:
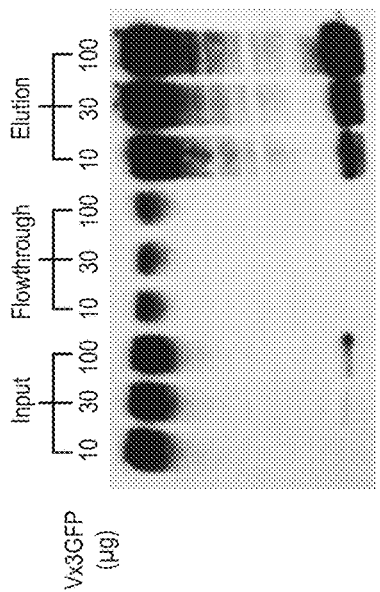
FIGS. 3C-3D are graphs of T cell stimulation by isolated ubiquitinylated protein loaded dendritic cells.

FIG. 3A schematically shows a GFP-Vx3(A7) fusion protein. Vx3 is a peptide comprising three relatively tight ubiquitin binding Vps27 UIM domains. Vx3 binds both Lys63 linked ubiquitin species and Lys48 linked ubiquitin species, though Lys63 linked ubiquitin species are bound with a higher specificity. GFP-Vx3(A7) may thus be used to bind and affinity-purify ubiquitinylated protein from cell lysates. GFP-Vx3(A7) also includes an N-Terminal poly-His tag that may be used to affinity purify the protein.

In one experiment, UbiLT3 cells were grown in culture, treated with 200 nM bortezomib for 24 hours, harvested, and lysed. 10, 30, or 100 µg of purified GFP-Vx3(A7) were added to UbiLT3 lysate and co-incubated overnight. Nickel resin was then added to the mixture and co-incubated overnight. The nickel resin was separated via centrifugation, with the supernatant reserved as a flow-through fraction. The nickel resin was then washed with a low-concentration imidazole solution, and bound protein then eluted with a high-concentration imidazole solution. FIG. 3B shows an example digital image of the input, flow-through, and elution fractions for 10, 30, and 100 µg of purified GFP-Vx3 (A7).

Figure 3D:
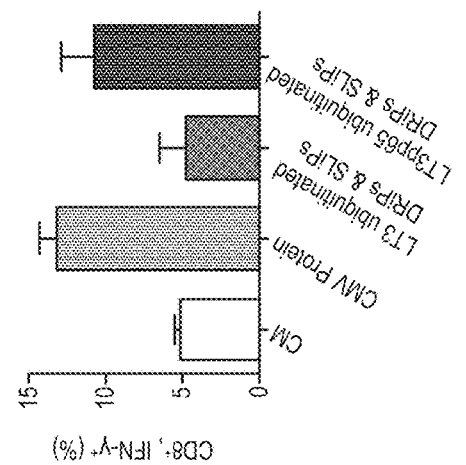
Figure 3C:
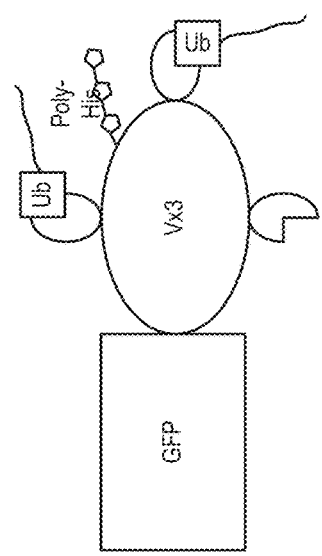

The isolated ubiquitinylated protein may then be presented to dendritic cells (DCs), which may then be used to cross-present antigen to T cells. In one experiment, human DCs were loaded with isolated ubiquitinylated protein from with UbiLT3 cells, or UbiLT3 cells engineered to express cytomegalovirus structural protein pp65 (UbiLT3pp65). Purified CMV protein was loaded onto DCs as a positive control, while medium alone (CM) was used as a negative control. DCs were loaded for 6 hours, and then expanded effector T cells were added and stimulated for 16 hours. T cells were then analyzed for IFN-γ production by intracellular staining and brefeldin-A treatment, followed by flow-cytometry. FIGS. 3C and 3D show that ubiquitinylated protein isolated from UbiLT3pp65 cells (LT3pp65), but not UbiLT3 control cells (LT3) was able to stimulate pp65-specific IFN-γ production in both $CD8^+$ T cells (FIG. 3C) and $CD4^+$ T cells (FIG. 3D). These results indicate that in addition to serving as a vaccine, isolated ubiquitinylated proteins may be used to in vitro monitor and evaluate immune responses to vaccines, cancer, and/or infection with specific pathogens, for example by loading isolated ubiquitinylated proteins derived from cells expressing a specific antigen onto dendritic cells, presenting the loaded dendritic cells to T cells harvested from a patient treated with a vaccine against the specific antigen, and then evaluating IFN-γ production by the harvested T cells.

Figure 4A:
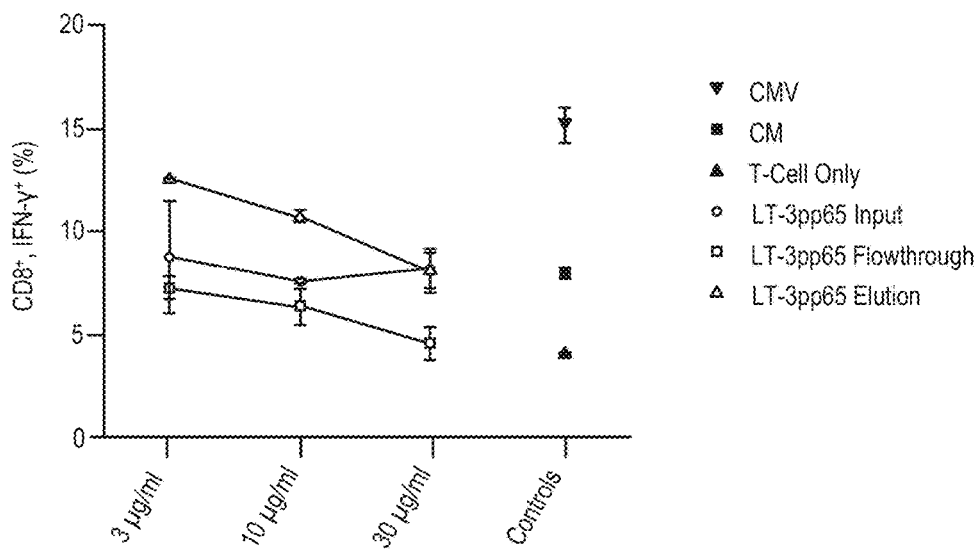
FIGS. 4A-4B are graphs of T cell stimulation by isolated ubiquitinylated protein loaded dendritic cells.
Figure 4B:
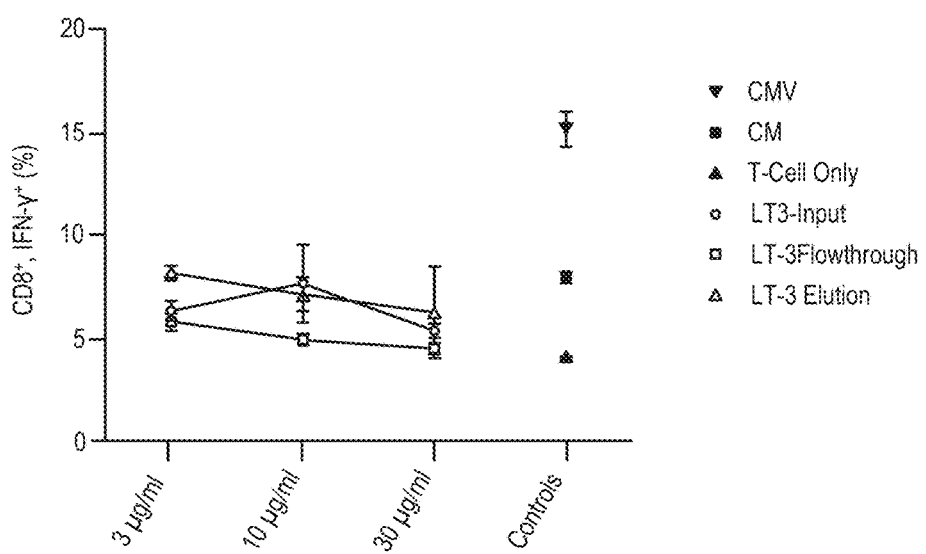

FIGS. 4A and 4B show graphs of similar experiments, where subsets of DCs were loaded with UbiLT3 and UbiLT3pp65 Ub-enriched, input, and flow-through fractions. As shown in FIG. 4A, for UbiLT3pp65, the eluted, isolated ubiquitinylated protein (elution) was more effective at stimulating IFN-γ production by CD8+ T cells than UbiLT3pp65 cell lysate alone (input). Minimal stimulation of pp65-specific T cells was induced by the flow-through fraction of the UbiLT3pp65 cell lysate or the Ub-enriched, input, and flow-through fractions of the UbiLT3 cell lysate.

Figure 5:
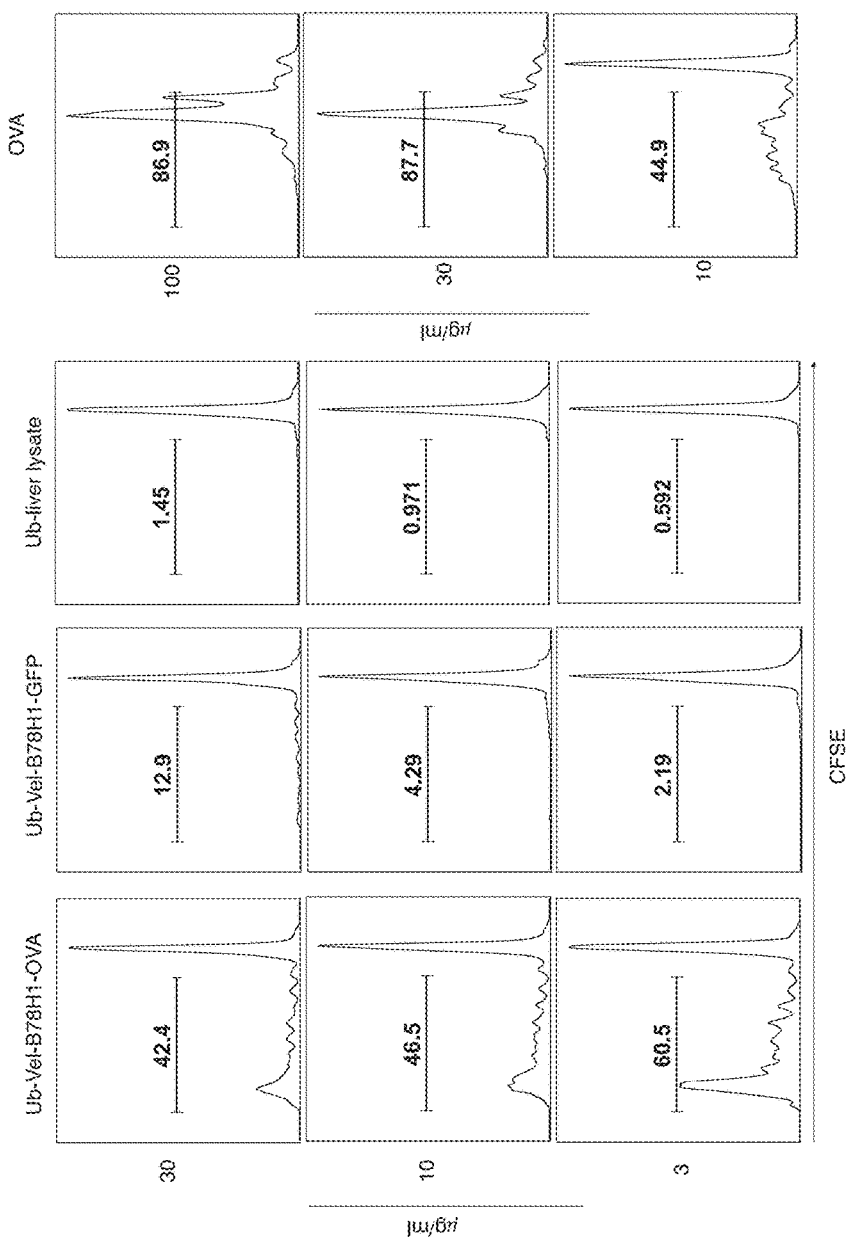
FIG. 5 is a graph showing OVA-specific T cell stimulation by isolated ubiquitinylated protein isolated from tumor cells.

FIG. 5 shows flow-cytometry distribution plots demonstrating that isolated ubiquitinylated protein is an efficient antigen resource for the cross-presentation of antigens to naïve $CD8^+$ T cells. B78/H1 cells, a class of murine B16 melanoma cells, were engineered to express R-GFP-OVA or R-GFP. The B78/H1 cells, were grown in culture, treated with bortezomib, harvested, and lysed. Ubiquitinylated protein was affinity purified from the B78/H1 lysate as well as from normal liver tissue lysate.

Murine Mutu-1940 DCs were loaded with aluminum nano-particles as well as purified ubiquitinylated protein (3, 10, or 30 µg) or purified OVA (10, 30, or 100 µg). The loaded DCs were then presented to CFSE-labeled OT-1 transgenic T cells. Activation of T cells was assessed by CFSE dilution following 6 days of co-incubation.

As shown in FIG. 5, DCs pulsed with isolated ubiquitinylated protein from antigen expressing cells (Ub-Vel-B78H1-OVA) were effective in stimulating OT-1 $CD8^+$ T cells, even at low antigen concentrations, whereas isolated ubiquitinylated protein from non-antigen expressing cells or normal liver tissue were not effective. Indeed, at lower concentrations (3 µg/ml) the isolated ubiquitinylated protein from Ub-Vel-B78H1-OVA stimulated OT-1 $CD8^+$ T cells with similar efficacy to purified OVA at a concentration of 10 µg/ml. The data shown in FIG. 5 is from one independent experiment, but was replicated with similar results (not shown).

These experiments demonstrate that isolated ubiquitinylated protein may be taken up by dendritic cells and cross-presented to T cells in the absence of other cellular components. Isolated ubiquitinylated protein may thus be utilized to prime an immune response in naïve T cells, either in vivo or in vitro.

EXAMPLE 2

Stimulation of Tumor-specific T Cells by Cross-presentation of Isolated Ubiquitinylated Proteins Historically, cancer vaccine induced T cells are rarely effective at eradicating tumors. The induced T cells, if they can recognize tumors and represent tumor-rejection antigens, often become sequestered, dissipate, undergo apoptosis, or merely fail to expand to levels capable of eradicating a tumor. By providing a broad range of potential tumor-rejection antigens that can be used to stimulate T cells against a spectrum of tumor rejection antigens, the therapeutic efficacy of the expanded T cells may be increased. Further, a broad immune response against a spectrum of tumor antigens will likely reduce the likelihood of tumors escaping from immune elimination, as the tumors would need to downregulate expression of a large number of antigens simultaneously.

Figure 6A:
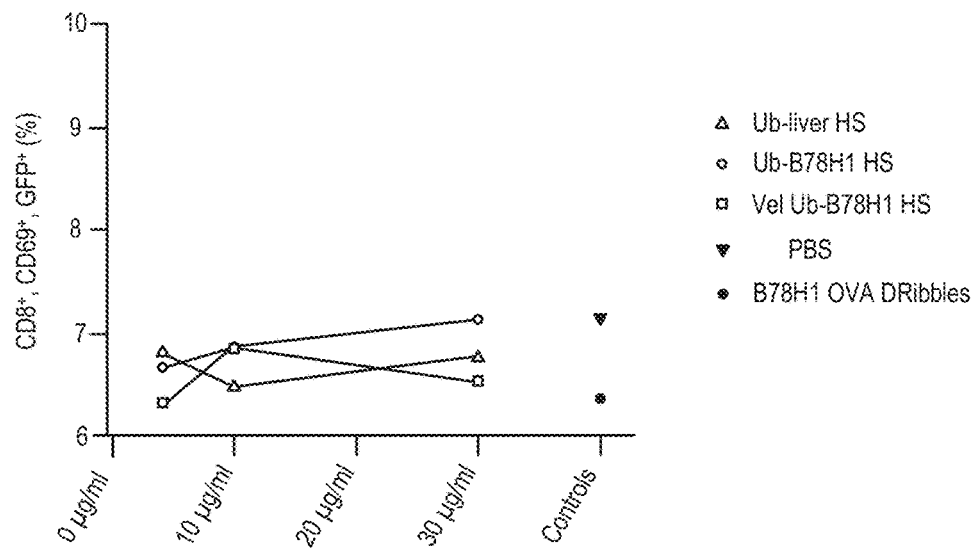
FIGS. 6A-6B are graphs of tumor-specific, DRibble primed T cell stimulation by isolated ubiquitinylated protein.
Figure 6B:
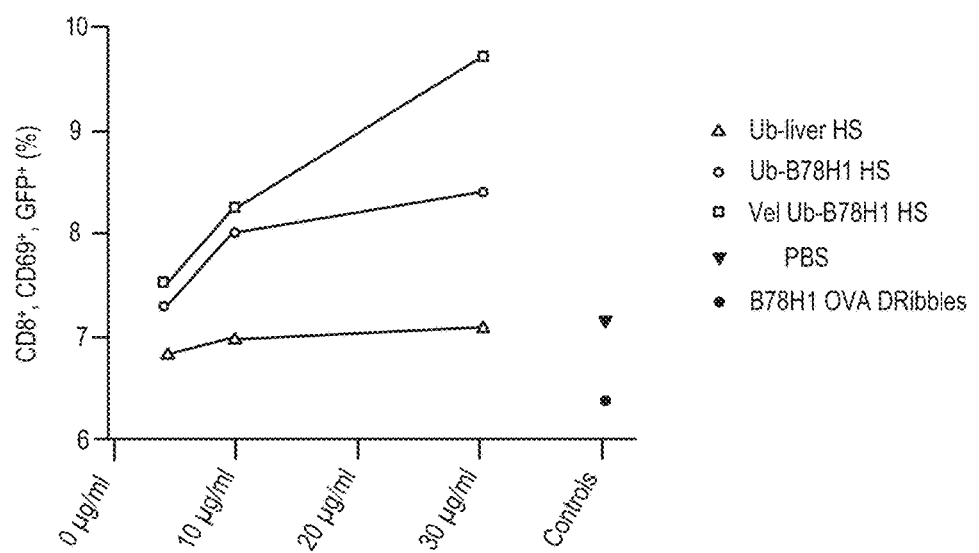

FIG. 6A-6B show graphs of tumor-specific, DRibble primed T cell stimulation by isolated ubiquitinylated protein. Nu77-GFPCre mice (a strain of C57BL/6 mice that express GFP in myeloid lineage cells in the spleen, as well as in T and B lymphocytes) were vaccinated with null vector (FIG. 6A) or DRibbles derived from B78/H1 cells (FIG. 6B). 7 days post-vaccination, the mice were sacrificed and splenocytes harvested. Mutu 1940 DCs were loaded with aluminum nanoparticles, as well as either PBS, or 5, 10, or 30 µg of isolated ubiquitinylated protein from normal liver cells (Ub-liver HS), 5, 10, or 30 µg of isolated ubiquitinylated protein from B78/H1 cells (Ub-B78H1 HS), 5, 10, or 30 µg of isolated ubiquitinylated protein from bortezomib treated B78/H1 cells (Vel Ub-B78H1 HS), or 5, 10, or 30 µg of DRibbles derived from B78/H1-OVA cells. The loaded DC's were then co-incubated with the isolated splenocytes. Activation of effector T cells was then examined via flow cytometry analysis for $CD8^+$, $CD69^+$, $GFP^+$ cells. For splenocytes isolated from previously vaccinated mice, a concentration dependent activation of effector T cells was seen for isolated ubiquitinylated protein from B78/H1 cells, and more dramatically for isolated ubiquitinylated protein from bortezomib treated B78/H1 cells.

This experiment suggests that isolated ubiquitinylated protein may be used as a vaccine booster. For example, an allogeneic autophagosome enriched composition may be provided to a tumor-bearing patient, followed by a composition comprising isolated ubiquitinylated protein derived from the patient's own primary tumor cells. In this way, the efficacy of the vaccine may be increased, as T cell expansion may be triggered following vaccination.

Figure 7:
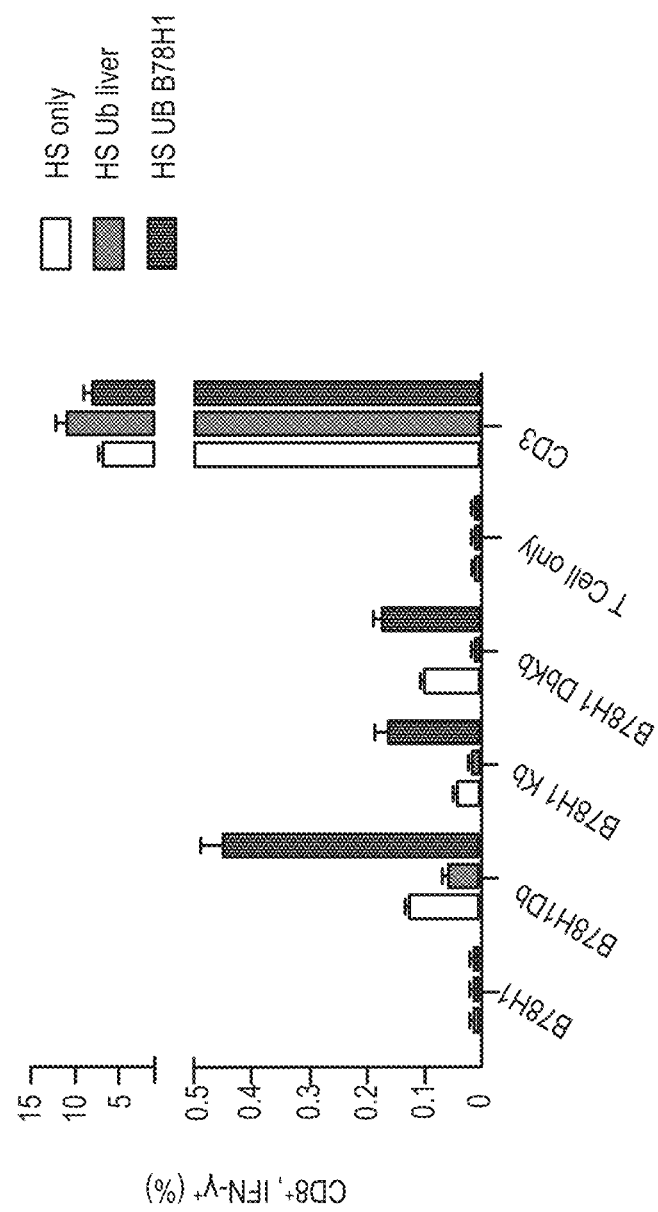
FIG. 7 is a graph of in vivo tumor-specific T cell induction mediated by isolated ubiquitinylated protein vaccination.

FIG. 7 is a graph of in vivo priming of tumor-specific T cells mediated by vaccination with isolated ubiquitinylated proteins. C57BL/6 mice were vaccinated with medium (HS), isolated ubiquitinylated protein from normal liver cells (HS Ub liver) or isolated ubiquitinylated protein from B78/H1 cells (HS Ub B78H1). 7 days post-vaccination, the mice were sacrificed and splenocytes harvested. Splenocytes were then co-incubated with B78/H1 cells, B78/H1 cells engineered to express H2-$D^b$ (B78H1Db), B78/H1 cells engineered to express H2-$K^b$ (B78H1Kb), B78/H1 cells engineered to express both H2-$D^b$ and H2-$K^b$ (B78H1$D^b K^b$), or anti-CD3 antibodies (CD3). T cell activation was then determined via flow cytometry for $CD8^+$, IFN-$\gamma^+$ cells.

As shown in FIG. 7, mice vaccinated with isolated ubiquitinylated protein from B78/H1 cells primed T cells that recognized B78/H1 cells engineered to express H2-$D^b$, H2-$K^b$, or both. This result suggests that vaccination with isolated ubiquitinylated protein from B78/H1 cells effectively primed in vivo T cells specific for that tumor type in an MHC-I restricted fashion.

EXAMPLE 3

Isolated Ubiquitinylated Proteins Stimulates Inflammatory Response

Figure 8:
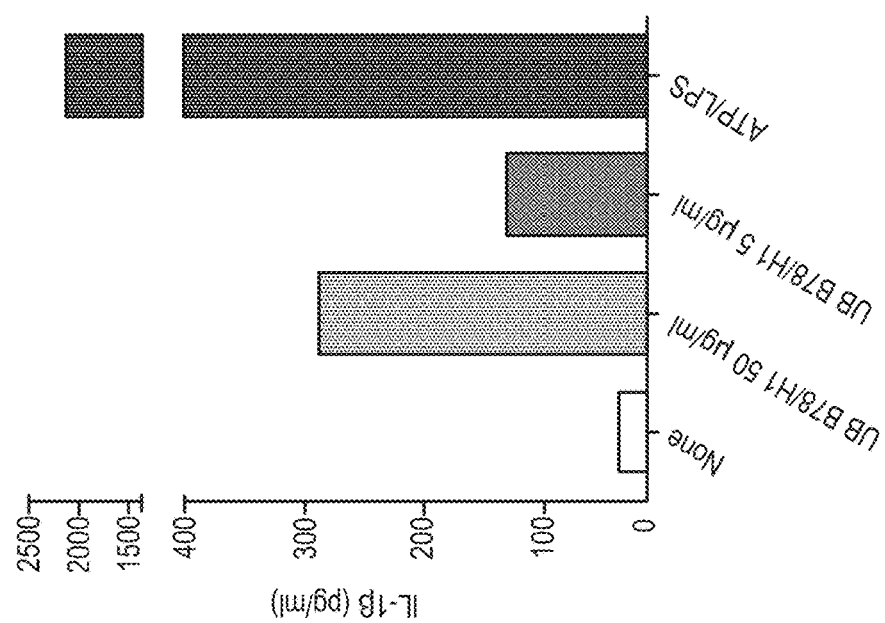
FIG. 8 is a graph of an inflammatory response induced by isolated ubiquitinylated proteins.
Figure 9B:
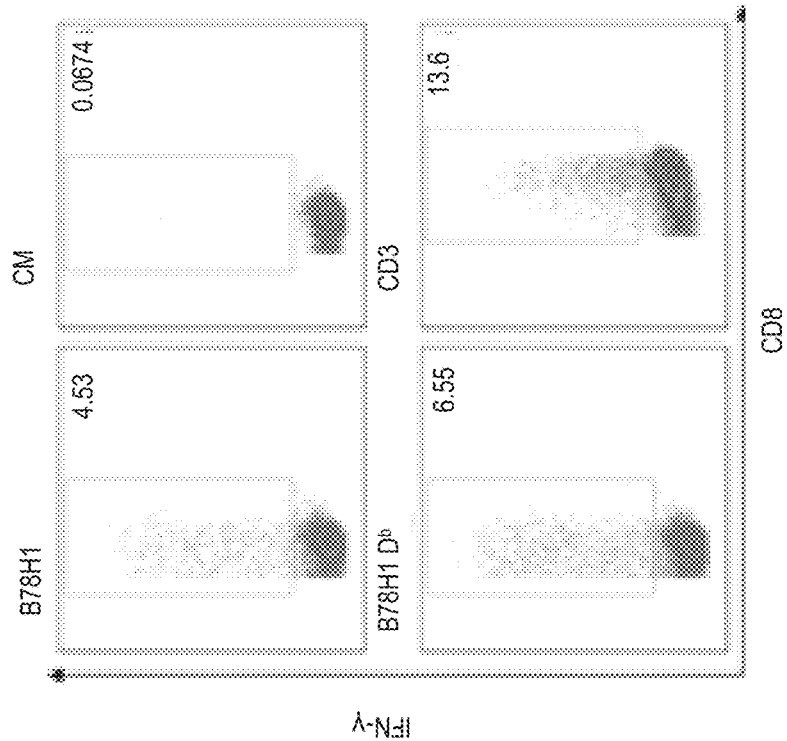
FIGS. 9A-9D show flow cytometry plots demonstrating MHC 1a dependent and independent CD8+ T cells can be cross-primed by isolated ubiquitinylated proteins.
Figure 9A:
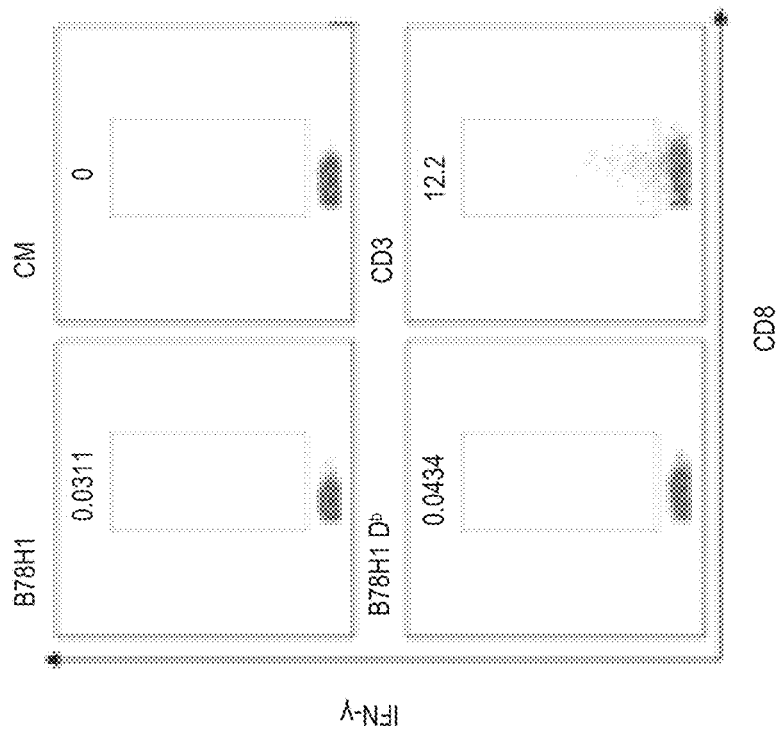
Figure 9D:
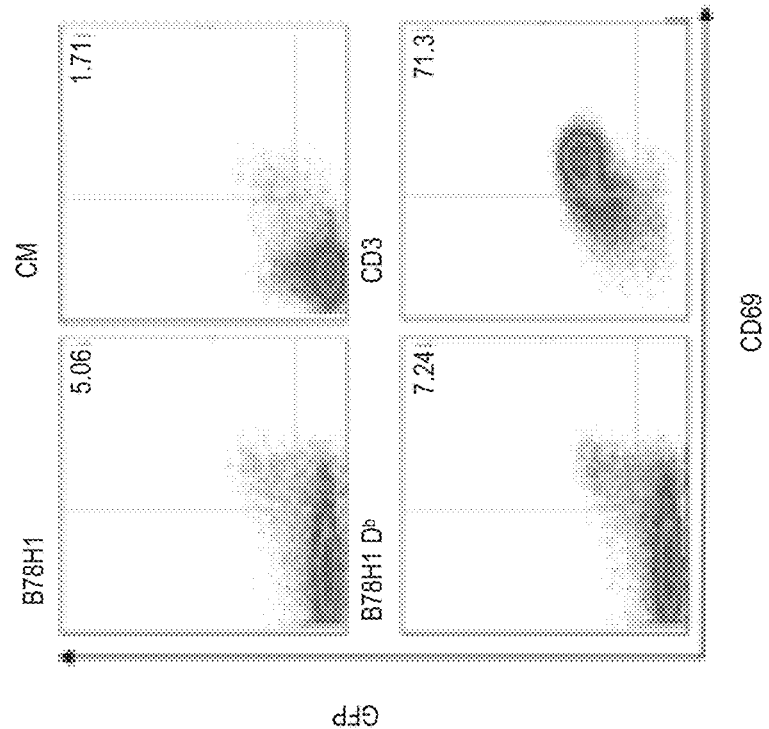
Figure 9C:
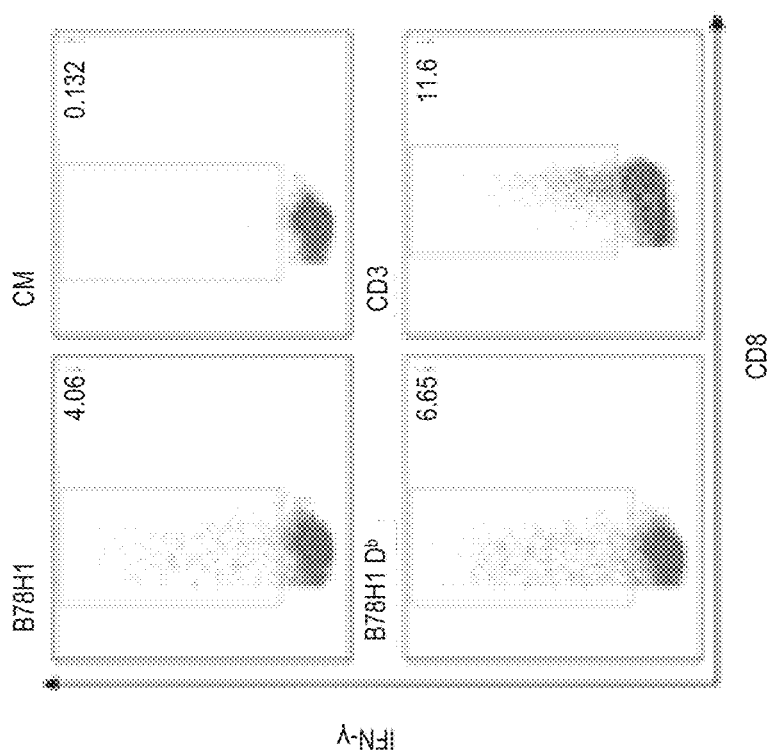

Immunological adjuvants rely on the immune inflammatory response in order to potentiate and/or modulate an immune response. FIG. 8 shows a graph of an inflammatory response induced by isolated ubiquitinylated proteins. Peripheral blood mononuclear cells (PBMCs) were seeded in a 96 well plate at $10^6$ cells/well. The PBMCs were then incubated with 5 mM ATP+10 ng/ml Lipopolysaccharide (ATP/LPS) or isolated ubiquitinylated proteins from B78/H1 cells at 5 µg/ml or 50 µg/ml overnight. The supernatant for each well was then removed and tested for IL-1β by ELISA. As shown in FIG. 8, IL-1β was stimulated in a concentration dependent manner by isolated ubiquitinylated protein from B78/H1 cells. IL-1β is a pro-inflammatory cytokine, and the production of this cytokine documents the inflammatory nature of the ubiquitinylated proteins. The induction of an inflammatory response is a common property of vaccine adjuvants and works to augment the development of a vaccine-specific immune response. The isolated ubiquitinylated protein may thus have both antigenic and adjuvant properties. By stimulating inflammation at the site of T cell action, a vaccine derived from isolated ubiquitinylated protein would provide an inflammatory response that may enhance the generation of vaccine-specific immune responses.

EXAMPLE 4

MHC Class 1a Dependent and Independent T Cell Cross-priming Mediated by Isolated Ubiquitinylated Protein One major mechanism for tumors to escape immune surveillance is to reduce or eliminate altogether the expression of MHC class 1a molecules. At the same time, non-classical MHC class 1b molecules are frequently up-regulated on tumor cells as a mechanism to escape elimination by NK cells or CTL. A vaccine that primes T cells that recognize tumor cells independent of MHC class 1a could thus widen the spectrum of rejection antigens that could be targeted by T cells, thus reducing the likelihood of tumor cells escaping immune elimination.

The B78/H1 clone of B16 melanoma cells has defective expression of classical MHC class I molecules (MHC class 1a) but retains expression of the non-polymorphic MHC class I molecules (MHC class 1b). FIGS. 9A-9D show flow cytometry plots demonstrating MHC class 1a dependent and independent CD8+ T cells can be cross-primed by isolated ubiquitinylated proteins. Nurr77GFP reporter mice were vaccinated with 15 µg of either DRibbles or isolated ubiquitinylated proteins from B78H1 melanoma cells. DRibbles were administered intra-nodally, while isolated ubiquitinylated proteins were administered sub-cutaneously in conjunction with alumina nanoparticles. The ability of primed $CD8^+$ T cells to recognize parental B78H1 cells and B78H1 cells transfected to express exogenous H2-$K^b$ or $D^b$ molecules was then analyzed. Injected or draining lymph nodes were collected 7-10 days after immunization and lymphocytes were stimulated with B78H1 or B7H1 tumor cells expressing H2-$D^b$ or $K^b$. The negative and positive controls were medium alone (CM) and anti-CD3 antibodies (CD3). Flow cytometry analysis was performed to determine the percentage of CD8+ T cells producing IFN-γ (9A-9C) or up-regulate GFP and CD69 expression (9D). Approximately 4% of $CD8^+$ T cells primed with either DRibbles (FIG. 9B) or Ub-proteins (FIG. 9C) could produce IFN-γ when stimulated ex vivo with MHC class 1a⁻ B78/H1. Expression of $D^b$ (and $K^b$ to a lesser extent) further increased the percentage of IFN-γ $CD8^+$ T cells. When mice were immunized with isolated ubiquitinylated proteins from normal mouse liver (FIG. 9A), no IFN-γ producing $CD8^+$ T cells were detected when simulated with either B78H1 or B78H-$D^b$ cells. Because B78H1 cells are TAP-2 deficient, these T cells recognize epitopes presented by a TAP-2-independent mechanism. Examining GFP expression revealed that the majority of B78H1 reactive IFN-γ producing CD8+ T cells are not restricted by MHC class 1a molecules.

EXAMPLE 5

Ubiquitinylated Protein as a Tumor Vaccine

While tumor-derived autophagosome based vaccines (such as DRibbles) may be used to generate a broader anti-tumor immune response than whole cell vaccines, isolating and repackaging the highly-immunogenic ubiquitinylated protein may allow for a more potent vaccine that includes subdominant, neo, and cryptic antigens capable of priming a different repertoire of T cells than those packaged within autophagosomes, which may be limited by the cellular components co-isolated during the autophagosome preparation process. Many of the classical murine tumor models (e.g. 4T1 or B16BL6-D5) are poorly immunogenic and difficult to treat. Spontaneous tumors may be even more difficult to treat. Recent data suggests that the number of mutations present in a tumor may affect its level of endogenous immunogenicity. As such, new, spontaneously arising tumors may have very few mutations and be even less immunogenic.

Figure 10:
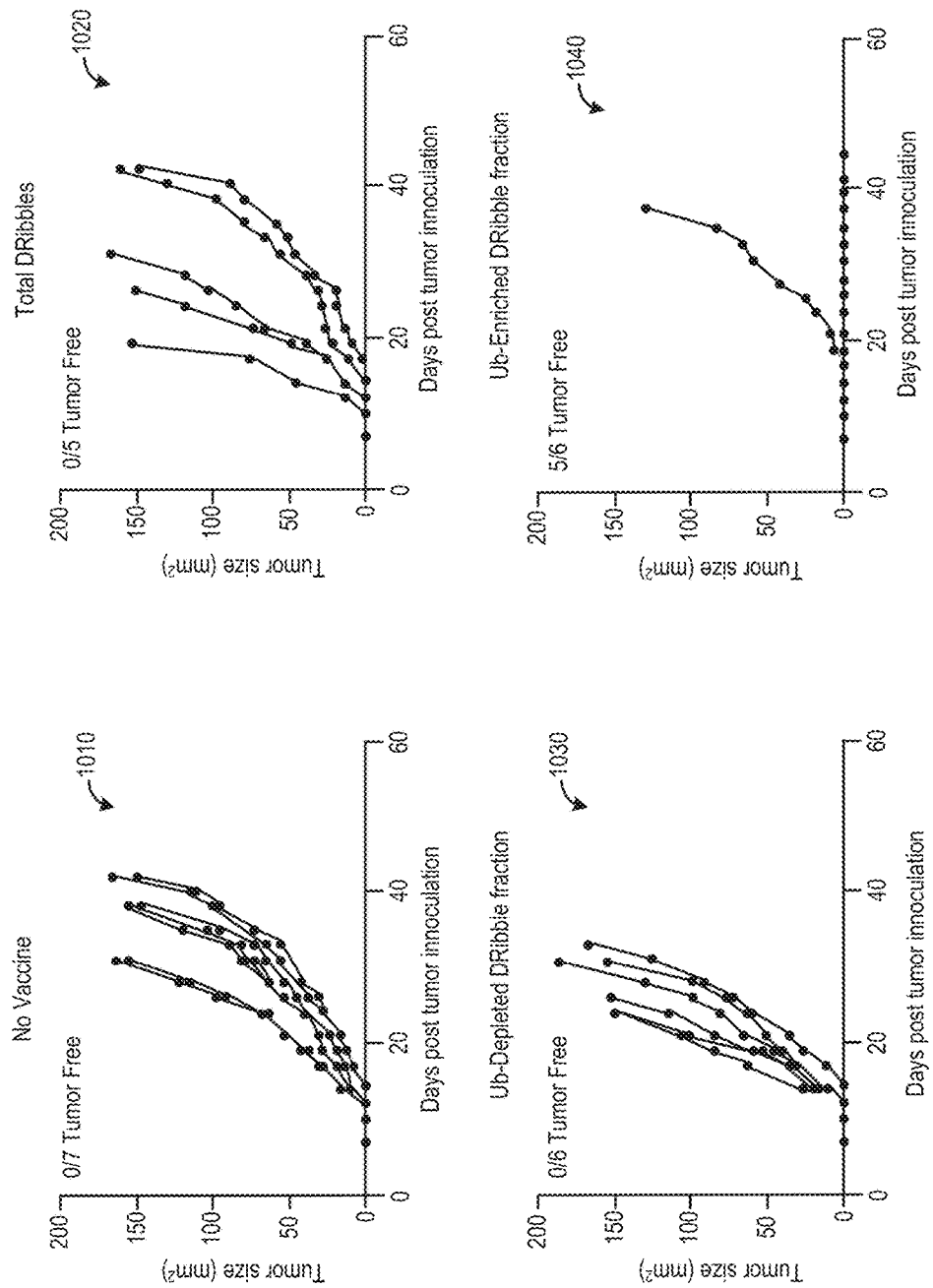
FIG. 10 shows survival plots for tumor-bearing mice vaccinated with isolated ubiquitinylated protein.

FIG. 10 shows survival plots for tumor-bearing mice vaccinated with isolated ubiquitinylated protein. Mice were challenged with a 4T1 mammary tumor, then received immunotherapy with medium (no vaccine, plot 1010), intact DRibbles derived from 4T1 cells (plot 1020), a 4T1 DRibble fraction depleted of ubiquitinylated protein (plot 1030), or ubiquitinylated protein isolated from 4T1 DRibbles (plot 1040). Mice were challenged with 25,000 viable 4T1 tumor cells grown in culture and harvested. On day 5 post-inoculation, the mice received immunotherapy that included 10 µg per node of one of the above stated vaccine classes. Mice received vaccine boosts with equivalent contents on days 7 and 9 post-inoculation.

For this experiment, DRibbles were derived from 4T1 cells. Briefly, cells were treated with Bortezomib (200 nmol/L) and ammonium chloride (10~20 mmol/L) for 24 hours. Cells and cellular debris were pelleted by centrifugation at 300×g for 7 minutes. DRibbles were dislodged from cells or clumps of cell debris by rigorous pipetting. The suspension was then centrifuged at 7500×g to pellet the DRibbles. Supernatant containing nanovesicles and exosomes was discarded.

A fraction of the isolated DRibbles were lysed in 5x-RIPA buffer on ice, and then sonicated to disrupt membranes. Membranes were removed from solution by centrifugation at 13,000×g for 12 minutes at 4° C. The resulting solution was diluted 1:10 in PBS. Commercially available S5a-linked beads were then used to capture ubiquitinylated protein from solution by incubating overnight at 4° C. S5a has a The S5a-linked beads were washed 2× in 90% PBS/10% cell lysis buffer. Protein bound to the S5a-linked beads was eluted in a solution containing 2M NaCl, pH 6.0 (phosphate) at 56° C. for 30 minutes. The elution was repeatedly dialyzed into PBS, then concentrated into a 1 mg/ml solution. Although S5a has a higher affinity for K-48 linked ubiquitin, both K-48 and K-63 linked ubiquitin species were detected in the eluate by western blot (not shown).

As shown in plot 1040, 5 of 6 mice vaccinated with the Ub-Enriched DRibble fraction were tumor-free 42 days after inoculation, while all of the mice in the control group, intact DRibble group, or Ub-Depleted DRibble fraction developed tumors. This result suggests that the ubiquitinylated protein contained within the DRibbles is critical to the therapeutic properties of the DRibble vaccine. By isolating the ubiquitinylated proteins, the vaccine can be concentrated, and may be made more efficient at stimulating anti-tumor activity.

EXAMPLE 6

Derivation of Vaccine from Cells Expressing Pathogen-associated Proteins

Another means for deriving target-specific ubiqitinylated protein is to insert the genome, or components of the genome of a specific human or animal pathogen into a cell line used to generate the ubiquitinylated proteins, for example, HIV. Isolation of ubiquitinylated proteins from cells expressing HIV proteins may be used as a vaccine to boost immunity and potentially clear HIV genomes. Such a vaccine may be used in combination with CMV vectors directed against this disease. In other scenarios, the genome, or components of the genome of a specific human pathogen (e.g. Mycobacterium tuberculosis or Ebola) may be inserted into a cell line used to generate the ubiquitinylated proteins. In other examples, the genome, or components of the genome of a specific animal pathogen (e.g. Porcine reproductive and respiratory syndrome virus (PRRSV) may be inserted into a cell line used to generate the ubiquitinylated proteins.

Figure 11:
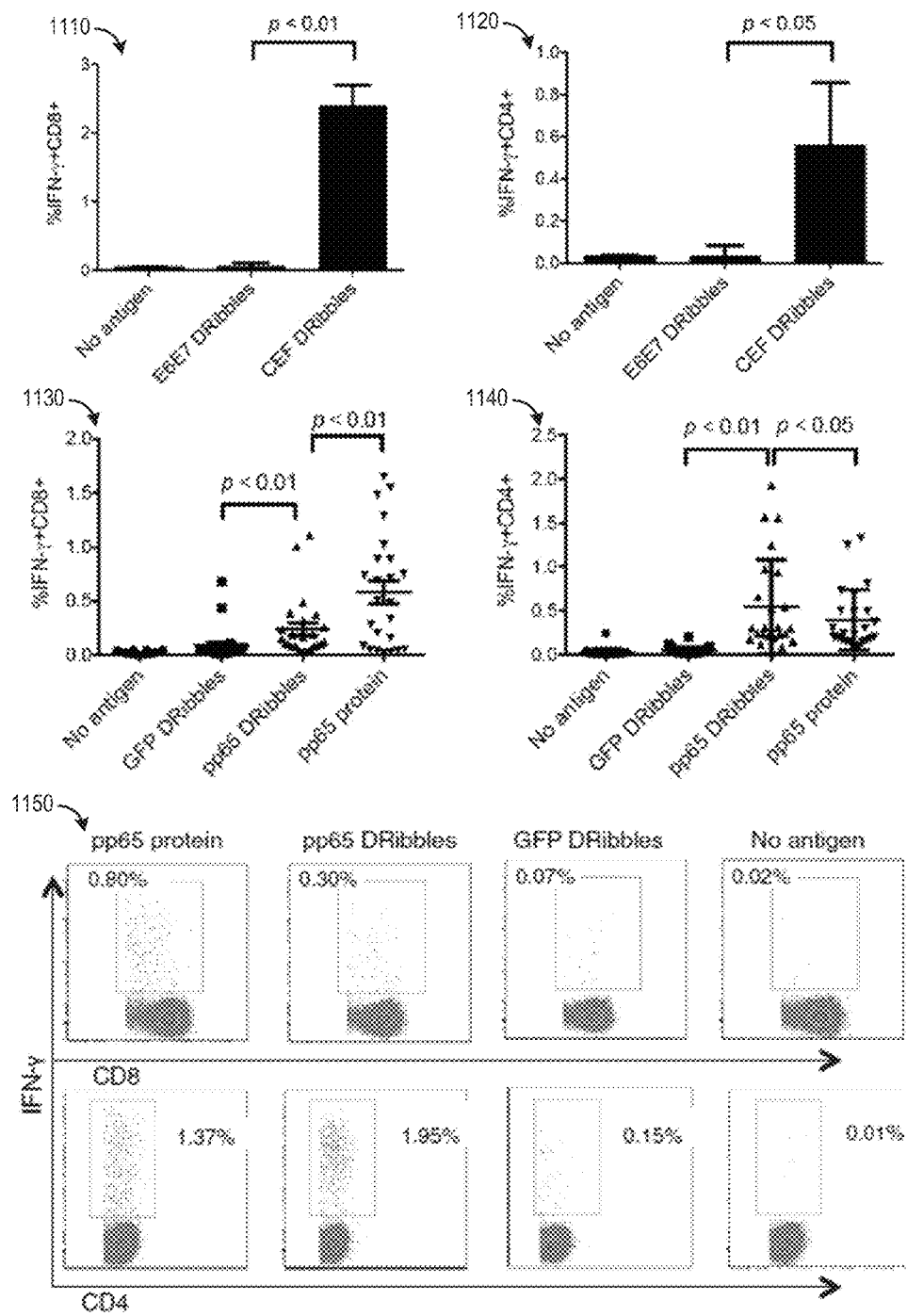
FIG. 11 shows graphs and plots demonstrating that DRibbles isolated from cells expressing CMV specific antigens efficiently carry and cross-present those antigens.

FIG. 11 shows graphs and plots demonstrating that DRibbles isolated from cells expressing CMV specific antigens efficiently carry and cross-present those antigens. Monocytes loaded with CEF-DRibbles stimulated more CD8+ T cells than control E6E7-DRibbles (2.4% vs 0.06%; $p<0.01$; plot 1110) and CD4+ T cells (0.56% vs 0.03%; $p<0.05$; plot 1120). Stimulation with E6E7-DRibbles did not increase the response beyond the frequency observed in the no antigen groups. These results showed that, when loaded onto monocytes, HEK 293 T derived DRibbles, cross-presented viral antigens to both antigen-specific CD8+ T cells and CD4+ T cells response. There was no apparent non-specific stimulation of memory T cells by DRibbles derived from HEK 293 T cells lacking the CEF antigenic peptides.

We also used DRibbles derived from the UbiLT3 cell line, which was derived from a patient with cancer. A line of UbiLT3 that expressed the pp65 protein of CMV was generated and used to prepare DRibbles as a source of CMV pp65 antigens to stimulate PBMCs from 24 donors. The percentage of IFN-γ+CD8+ T cells and IFN-γ+CD4+ T cells were calculated following intracellular staining protocol described above. The mean percentage of IFN-γ+CD8+ T cells was 0.24% for the UbiLT3pp65 DRibbles-stimulated group compared to 0.08% in the paired group of T cells treated with control UbiLT3 GFP DRibbles ($p<0.01$; plot 1130, flow charts 1150). The mean percentage of CD4+ T cells that produced IFN-γ upon pp65 DRibbles stimulation was 0.54%, vs 0.04% following stimulation with control DRibbles ($p<0.01$; plot 1140, flow charts 1150) Compared to purified recombinant CMV pp65 protein, UbiLT3pp65 DRibbles were better stimulators of memory CD4+ T-cells (0.54% vs 0.39%, $p<0.05$, FIG. 2D,E) but less stimulatory to memory CD8+ T-cells (0.24% vs 0.58%, $p<0.01$, FIG. 2C,E). These data show that DRibbles from HEK293T cells and UbiLT3 cells are potent immunogens for antigen-specific activation of CD8+ T-cells and CD4+ T cells when loaded onto elutriated monocytes or added directly to human PBMCs.

These results indicate that expressed viral proteins are shunted into DRibbles, where they may be used as antigens for cross-presentation. By isolating ubiquitinylated protein from cells expressing viral proteins, an immunogen with increased potency may be derived. Cell types expressing a variety of antigens, including tumor antigens, viral antigens, bacterial antigens, and other pathogen antigens may be cultured and inhibited from degrading proteins via the proteasome. Ubiquitinylated protein may then be isolated from these cells for use as vaccine, immune booster, T-cell primer, immunological monitoring reagent, or other immunogenic or therapeutic compound.

The experimental data and methods presented above may enable one or more compositions and one or more methods. In one example, a composition configured to induce a specific immune response in a mammal, comprising isolated ubiquitinylated proteins in solution in absence of membrane bound organelles, the isolated ubiquitinylated proteins containing one or more specific antigens, and further containing a threshold quantity of polyubiquitinylated short-lived proteins (SLiPs) and polyubiquitinylated defective ribosomal products (DRiPs) is provided. The threshold quantity of SLiPs and DRiPs may be a quantity sufficient to prime an immune response in naïve T cells in vivo and/or in vitro. The threshold quantity of SLiPs and DRiPs may be a quantity sufficient to stimulate proliferation of tumor-specific T cells. The threshold quantity of SLiPs and DRiPs may be a quantity sufficient to load dendritic cells in vivo or in vitro such that antigen may be cross-presented to T cells. The threshold quantity of SLiPs and DRiPs may be a quantity sufficient to stimulate cross-priming of T cells independent of MHC class 1a. The threshold quantity of SLiPs and DRiPs may be a quantity sufficient to stimulate anti-tumor activity in vivo. The threshold quantity of SLiPs and DRiPs may further be a quantity sufficient to stimulate an inflammatory response in vivo.

The isolated ubiquitinylated proteins may be affinity-purified from tumor-derived cells grown in culture. The tumor-derived cells may be inhibited from degrading ubiquitinylated proteins via a proteasome while being grown in culture, for example by use of a proteasome inhibitor (e.g. bortezomib). In some examples, the tumor-derived cells may be inhibited from degrading ubiquitinylated proteins via a lysosome while being grown in culture, for example by use of a lysosome inhibitor.

The tumor-derived cells may be derived from a mammalian tumor. In some examples, the tumor-derived cells may be primary culture cells derived from a tumor in the mammal. In some examples, the tumor-derived cells may be derived from tumor cell lines. The tumor-derived cells may be engineered to express one or more specific antigens not endogenous to the tumor-derived cells, such as tumor-specific antigens, viral antigens, bacterial antigens, pathogen antigens, etc.

In another example, a method for producing an immunogenic reagent, comprising: inhibiting proteasomal degradation of ubiquitinylated proteins in tumor-derived cells growing in culture; and isolating ubiquitinylated proteins in absence of membrane bound organelles from the tumor-derived cells grown in culture, the isolated ubiquitinylated proteins containing one or more specific antigens, and further containing a threshold quantity of polyubiquitinylated short-lived proteins and polyubiquitinylated defective ribosomal products is provided. The method may further comprise lysing the tumor cells; affinity-purifying ubiquitinylated protein from a resulting cell lysate with a recombinant polyubiquitin binding peptide; and eluting the ubiquitinylated protein from the recombinant polyubiquitin binding peptide.

In yet another example, a method of inducing a specific immune response in a mammal, comprising: providing a first composition comprising isolated ubiquitinylated proteins in solution, the isolated ubiquitinylated proteins containing one or more specific antigens, and further containing a threshold quantity of polyubiquitinylated short-lived proteins and polyubiquitinylated defective ribosomal products; and cross-presenting the one or more specific antigens to T cells is provided. The method may further comprise loading dendritic cells with the first composition in vitro to generate loaded dendritic cells; and cross-presenting antigen from the loaded dendritic cells to T cells. The antigen may be cross-presented from the loaded dendritic cells to T cells in vivo or in vitro. The first composition is injected into the mammal sub-cutaneously, or administered intra-nodally, intra-nasally, intra-veinously, or by any other suitable means. The first composition may be injected into the mammal after a duration following an injection of a second composition capable of inducing a specific immune response in the mammal. The second composition is an allogeneic autophagosome-enriched composition, such as a DRibble vaccine. The specific immune response may target classical and/or non-classical MHC restricted antigens.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A composition configured to induce a specific immune response to a tumor or cancer in a mammal, comprising:
   isolated ubiquitinylated proteins in solution in absence of double membranes, the isolated ubiquitinylated proteins isolated from cells of the tumor or cancer via a step of inhibiting the ubiquitinylated proteins from being degraded, a step of removing cellular debris, a step of isolating autophagosomes, a step of disrupting the autophagosomes to remove the double membranes, and then a step of affinity-purifying the ubiquitinylated proteins,
   such that the composition contains one or more p62 bound antigens the p62 bound antigens comprising a threshold quantity of K48 or K63 linked polyubiquitinylated short-lived proteins and K48 or K63 linked polyubiquitinylated defective ribosomal products, from the tumor or cancer.

2. The composition of claim 1, wherein the isolated ubiquitinylated proteins are affinity-purified from the cells of the tumor or cancer-grown in culture.

3. The composition of claim 2, wherein the cells of the tumor or cancer are engineered to express one or more specific antigens not endogenous to the cells of the tumor or cancer.

4. The composition of claim 3, wherein the one or more specific antigens not endogenous to the cells of the tumor or cancer include a viral antigen.

5. The composition of claim 3, wherein the one or more specific antigens not endogenous to the cells of the tumor or cancer include a bacterial antigen.

6. The composition of claim 1, wherein the threshold quantity includes a quantity sufficient to prime an immune response in naïve T cells in vivo and/or in vitro.

7. The composition of claim 1, wherein the threshold quantity includes a quantity sufficient to stimulate proliferation of T cells specific to the tumor or cancer.

8. The composition of claim 1, wherein the threshold quantity includes a quantity sufficient to load dendritic cells in vivo or in vitro to cross-present antigen to T-cells.

9. The composition of claim 1, wherein the threshold quantity includes a quantity sufficient to stimulate cross-priming of T cells independent of major histocompatibility complex class 1a.

10. The composition of claim 1, wherein the threshold quantity includes a quantity sufficient to stimulate anti-tumor activity in vivo.

11. The composition of claim 1, wherein the threshold quantity includes a quantity sufficient to stimulate an inflammatory response in vivo.

* * * * *